United States Patent
Sangirardi et al.

(10) Patent No.: US 10,271,551 B2
(45) Date of Patent: Apr. 30, 2019

(54) PRESERVATIVE COMPOSITION FOR WET WIPES

(71) Applicant: Lonza Inc., Allendale, NJ (US)

(72) Inventors: Angela Marie Sangirardi, Saddle Brook, NJ (US); Susan Ahrendt Mills, Ringwood, NJ (US); Vito Thomas Cataldo, Hoboken, NJ (US)

(73) Assignee: Lonza Inc., Morristown, NJ (US)

( * ) Notice: Subject to any disclaimer, the term of this patent is extended or adjusted under 35 U.S.C. 154(b) by 0 days.

(21) Appl. No.: 15/629,335

(22) Filed: Jun. 21, 2017

(65) Prior Publication Data

US 2017/0367331 A1    Dec. 28, 2017

Related U.S. Application Data

(60) Provisional application No. 62/353,216, filed on Jun. 22, 2016.

(51) Int. Cl.
| | |
|---|---|
| *C11D 17/04* | (2006.01) |
| *A01N 43/16* | (2006.01) |
| *A01N 25/08* | (2006.01) |
| *A01N 37/10* | (2006.01) |
| *C11D 3/48* | (2006.01) |
| *C11D 7/26* | (2006.01) |

(52) U.S. Cl.
CPC ............. *A01N 43/16* (2013.01); *A01N 25/08* (2013.01); *A01N 37/10* (2013.01); *C11D 3/48* (2013.01); *C11D 7/263* (2013.01); *C11D 7/265* (2013.01); *C11D 7/267* (2013.01); *C11D 17/049* (2013.01)

(58) Field of Classification Search
None
See application file for complete search history.

(56) References Cited

U.S. PATENT DOCUMENTS

| | | | |
|---|---|---|---|
| 5,539,001 | A | 7/1996 | Waldmann-Laue et al. |
| 6,482,423 | B1 | 11/2002 | Beerse et al. |
| 7,537,776 | B1 | 5/2009 | Beilfuss et al. |
| 8,784,910 | B2 | 7/2014 | Lutz et al. |
| 9,060,952 | B2 | 6/2015 | Nunez et al. |
| 9,096,821 | B1 * | 8/2015 | Hope ........................ C11D 1/65 |
| 2004/0047905 | A1 * | 3/2004 | Padlo ................... A61K 8/0208 424/465 |
| 2006/0093634 | A1 * | 5/2006 | Lutz ........................ A61K 8/365 424/401 |
| 2007/0141127 | A1 | 6/2007 | Casas-Sanchez et al. |
| 2008/0234173 | A1 | 9/2008 | Warr et al. |
| 2009/0004122 | A1 | 1/2009 | Modak |
| 2011/0086918 | A1 | 4/2011 | Ciccognani et al. |
| 2011/0152383 | A1 | 6/2011 | Schmaus et al. |
| 2012/0201902 | A1 | 8/2012 | Modak et al. |
| 2014/0004163 | A1 | 1/2014 | Mundschau et al. |
| 2014/0171512 | A1 | 6/2014 | Kloeppel et al. |
| 2015/0125502 | A1 | 5/2015 | Colurciello et al. |
| 2015/0189872 | A1 | 7/2015 | Gradtke et al. |
| 2016/0213585 | A1 | 7/2016 | Sangirardi et al. |

FOREIGN PATENT DOCUMENTS

| | | | |
|---|---|---|---|
| CN | 103919689 | A * | 7/2014 |
| EP | 0763341 | | 3/1997 |
| JP | 2008295837 | A * | 12/2008 |
| WO | WO 2013066403 | A1 | 5/2013 |
| WO | WO 2014207179 | A1 | 12/2014 |

OTHER PUBLICATIONS

Traul et al., Review of the toxicologic properties of medium-chain triglycerides; Food Chem Toxicol. Jan. 2000; 38(1): 79-98.
Anonymous: Mikrokill TM ECT, Internet Citation, Jan. 29, 2010, pp. 1-8, XP002712123, Retrieved from the Internet: URL: http://az290931,Vo.msecnd.Net/www.in-cosmetics.com/_novadocuments/2198x$query$xvx$eq$x634484823552730000 [retrieved on Sep. 11, 2013] Figure 1, p. 5, table 1.
Lonza Product Information Geogard™Ultra, Multifunctional specialty additive for cosmetics and toiletries, accepted under Natural and Organic cosmetics standards of Ecocert as well as Soil Association and NaTrue., Lonza Life Science Ingredients-Microbial Control Europe, pp. 1-7, dated Jun. 17, 2011.
PCT/US2017/038550 International Search Report and Written Opinion, dated Aug. 25, 2017, 12 pages.

* cited by examiner

*Primary Examiner* — Robert A Wax
*Assistant Examiner* — Melissa S Mercier
(74) *Attorney, Agent, or Firm* — Dority & Manning, P.A.

(57) ABSTRACT

A wiping composition and a wiping product containing the composition are disclosed. The wiping composition contains a combination of an antimicrobial agent with a preservative enhancing agent that not only provides antiseptic properties when applied to an adjacent surface, but also is well suited to preserving the substrate that is used to apply the composition. In particular, the composition has been unexpectedly found to inhibit or destroy bacteria, particularly *Burkholderia cepacia*, even when the active ingredients are used at extremely low levels.

23 Claims, No Drawings

PRESERVATIVE COMPOSITION FOR WET WIPES

RELATED APPLICATIONS

The present application is based on and claims priority to U.S. Provisional Patent application Ser. No. 62/353,216, filed on Jun. 22, 2016, which is incorporated herein by reference.

BACKGROUND

Wet wipes, such as those used for cosmetic removal, for cleaning surfaces, for use with infants during diaper changes, for wiping ones hands, and the like, often contain wiping compositions formulated for effective cleaning purposes. Various different methods and techniques are available for applying these wiping compositions to adjacent surfaces. For instance, in certain applications, the wiping composition is first applied to a wiping product which is then applied to an adjacent surface or object. In one embodiment, disposable wipes are saturated with the wiping composition. Presaturated wipes are very convenient for use in numerous applications, such as for disinfecting surfaces or for cleaning the skin of an infant, child, or adult. These presaturated wipes are particularly useful in on-the-go applications, such as in cars or public spaces where traditional cleaning methods, such as soap and water, are not available.

One problem that has become more prevalent in the use of presaturated wipes and other similar substrates is the inability to protect the substrate or wipe from microbial contamination. More particularly, even though the substrate is saturated with a wiping composition, many commonly used wiping solutions, including anti-microbial compositions, are not effective against various microorganisms that are known to attack wiping substrates, particularly wiping substrates containing cellulose.

For example, *Burkholderia cepacia* (*B. cepacia*), a group of complex bacteria that can be composed of at least 18 different bacteria species, can be found in soil and water and is known to contaminate natural substrates, particularly substrates containing cellulose, including wiping substrates such as wet wipes. A gram-negative bacteria, *B. cepacia* is extremely resistant to many antiseptics and antibacterial compositions. Other microorganisms that may contaminate and/or attack wiping substrates include *Staphylococcus aureus*, *Escherichia coli*, *Pseudomonas aeruginosa*, *Candida albicans*, and *Aspergillus brasiliensis*.

Recently, the problems associated with protecting and preserving wipe substrates from contamination has been exacerbated by the trend to use naturally occurring antimicrobial agents in preservatives. Thus, a need exists for a wiping composition comprising a preservative composition that can serve as a preservative for the substrate that is used to apply the wiping composition.

SUMMARY

In general, the present disclosure is directed to a wiping product, such as a pre-moistened wiper. The wiping product, for instance, may comprise a cosmetic wet wipe, a baby wet wipe, or other similar product. The wiping product generally includes a substrate containing natural fibers, synthetic fiber or a mixture thereof. Natural fibers often include cellulose, such as cellulosic fibers. In accordance with the present disclosure, a wiping solution is applied to and/or impregnated into the wet wipe that not only facilitates wiping of an adjacent surface or object, but also is formulated so as to protect the substrate itself from microbial contamination. In one embodiment, for instance, the wiping solution is formulated so as to preserve the substrate against microorganisms, particularly *Burkholderia cepacia*. In this regard, in one embodiment, the present disclosure is also directed to a wiping composition effective against *Burkholderia cepacia*.

In one embodiment, the present disclosure is directed to a wiping product comprising a liquid absorbent substrate, the liquid absorbent substrate may comprise a nonwoven web containing cellulose fibers. The cellulose fibers, for instance, may comprise pulp fibers. Examples of nonwoven webs used to produce the liquid absorbent substrate include coform webs, airlaid webs, hydroentangled webs, and the like. In accordance with the present disclosure, the liquid absorbent substrate contains a wiping composition. The wiping composition comprises a preservative composition comprising a gluconolactone, a benzoic acid or salt thereof, and a preservative enhancing agent.

In accordance with the present disclosure, the preservative enhancing agent is selected such that when combined with the gluconolactone and the benzoic acid or salt thereof, the resulting composition is capable of inhibiting or destroying microorganisms, such as *Burkholderia cepacia*. The preservative enhancing agent, for instance, may comprise a phenolether, an organic acid, or a salt of an organic acid. When using an organic acid or a salt of an organic acid, the preservative enhancing agent can have a carbon chain length of from about 6 carbon atoms to about 8 carbon atoms. The preservative enhancing agent may comprise a cyclic compound or an acyclic compound. Particular examples of preservative enhancing agents in accordance with the present disclosure are phenoxyethanol, sodium dehydroacetate, potassium sorbate, and the like, and mixtures thereof.

The wiping composition of the present disclosure is capable of protecting a liquid absorbent substrate against attack by microorganisms even when the preservative enhancing agent, benzoic acid or salt thereof, and/or the gluconolactone are present in the wiping composition at extremely low amounts. For instance, the preservative enhancing agent can be present in the wiping composition in an amount less than about 0.5%. The gluconolactone can be present in the wiping composition in an amount from about 0.75% to about 0.2% by weight. The benzoic acid or salt thereof can be present in the wiping composition in an amount from about 0.5% to about 0.05% by weight. It has been discovered that the combination of the gluconolactone with the preservative enhancing agent and the benzoic acid or salt thereof is effective against microorganisms such as *Burkholderia cepacia* even at the above low amounts.

In one embodiment, the preservative enhancing agent and the gluconolactone can be present in the wiping composition at a weight ratio of from about 5:1 to about 1:5, such as from about 2:1 to about 1:2, such as from about 1.5:1 to about 1:1.5.

The wiping composition can contain further ingredients and constituents. For instance, the composition can contain a solvent, such as water and/or an organic solvent. The antimicrobial composition may further contain one or more surfactants, chelators, builder salts, dyes or fragrances.

The present disclosure is also directed to a wiping composition containing a preservative comprising a gluconolactone in combination with a benzoic acid or salt thereof and a preservative enhancing agent as described above.

Other features and aspects of the present disclosure are discussed in greater detail below.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to a wiping composition that is not only well suited to wiping an adjacent surface when carried within a substrate, but is also capable of protecting the substrate itself against contamination from microorganisms. By inhibiting and preventing the growth of microorganisms on the substrate, no unwanted microorganisms are transferred to a surface while the surface is being wiped with the composition. The present disclosure is also directed to a wiping product comprising a liquid absorbent substrate containing the wiping composition described above.

Many wiping products, particularly cosmetic and baby wet wipes, are particularly difficult to preserve from microbial contamination, especially when the wiping product is made from natural substrates, such as those composed primarily of cellulose. Protecting the wiping product from contamination against various microorganisms, particularly *Burkholderia cepacia*, has been found to be problematic, especially when the substrate and the wiping solution are made from natural ingredients. The present disclosure, however, is directed to a wiping composition that is particularly formulated not only to comprise a gentle wiping solution for wiping adjacent surfaces, but is also formulated to preserve the substrate to which the composition is applied. Of particular advantage, it was discovered that by using relatively minor amounts of particular components in conjunction with each other can result in a wiping composition or solution that has dramatically and unexpectedly better preservative characteristics against many microorganisms, particularly *B. cepacia*.

In one embodiment, the present disclosure is directed to a wiping composition comprising a preservative composition, wherein the preservative composition comprises a gluconolactone in combination with a benzoic acid or salt thereof and a preservative enhancing agent. The preservative enhancing agent has been found to synergistically work with gluconolactone and the benzoic acid or salt thereof in producing a gentle and mild wiping composition that can also protect the substrate to which the composition is applied. Gluconolactone has been used in the past in wiping solutions for personal care wipes. In fact, gluconolactone is extremely mild and generally safe to use. The preservative enhancing agent of the present disclosure, however, has been found to work with gluconolactone and the benzoic acid or salt thereof in a manner where gluconolactone levels can be minimized while providing dramatic and unexpected efficacy against microorganisms such as *B. cepacia*.

In accordance with the present disclosure, the preservative enhancing agent used in conjunction with the gluconolactone and the benzoic acid or salt thereof can comprise a phenolether, an organic acid, or a salt of an organic acid, wherein the organic acid or the salt of an organic acid has a carbon chain length of from about 5 carbon atoms to about 8 carbon atoms, such as from 6 carbon atoms to 8 carbon atoms.

As described above, the present disclosure is generally directed to combining a gluconolactone with a benzoic acid or salt thereof and a preservative enhancing agent in order to provide a wiping composition that not only has antiseptic properties but is also capable of protecting a substrate used to apply the wiping composition to a surface from various pathogens. In one embodiment, the preservative enhancing agent comprises a phenolether. For instance, the phenolether may comprise a phenoxyalkanol, such as phenoxyethanol. Phenoxyethanol is a natural substance and can be found in green tea and chicory.

In an alternative embodiment, the preservative enhancing agent may comprise an organic acid or a salt of an organic acid. More particularly, the organic acid or the salt of an organic acid may have a carbon chain length of from about 5 carbon atoms to about 8 carbon atoms, such as from 6 carbon atoms to 8 carbon atoms. The organic acid or the salt of an organic acid can be cyclic or acyclic. In one embodiment, for instance, the preservative enhancing agent may comprise dehydroacetic acid or a metal salt of dehydroacetic acid. For example, in one embodiment, the preservative enhancing agent may comprise sodium dehydroacetate. Dehydroacetic acid is a pyrone derivative. In one embodiment of the present disclosure, the salt of the dehydroacetic acid, such as sodium dehydroacetate, is used in the formulation due to greater water solubility. Sodium dehydroacetate is known to be incompatible with some oxidizing agents. Sodium dehydroacetate, however, has been found to be compatible with gluconolactone and, in fact, has been found to be effective against *B. cepacia* when combined with gluconolactone even at relatively low concentrations.

In yet another embodiment of the present disclosure, the preservative enhancing agent comprises sorbic acid or a salt of sorbic acid. For example, in one embodiment, the preservative enhancing agent may comprise potassium sorbate. Potassium sorbate can be found in dry meat products and dried fruit and is a naturally occurring material. Thus, potassium sorbate is recommended as safe by the Food and Drug Administration. When used in the present disclosure and combined with a gluconolactone and a benzoic acid or salt thereof, potassium sorbate has been found to unexpectedly control the growth of the bacteria, *B. cepacia*. This result is surprising since potassium sorbate is typically known as a fungicide. Although the mechanism is unknown, it has been discovered that potassium sorbate in combination with gluconolactone and a benzoic acid or salt thereof can control the growth of various bacteria, even when present in relatively minor amounts.

In still another embodiment, the preservative enhancing agent may comprise further amounts of benzoic acid or a salt of benzoic acid or may comprise salicylic acid or a salt of salicylic acid.

In one embodiment, one or more preservative enhancing agents can be combined and used in conjunction with the gluconolactone and the benzoic acid or salt thereof. For example, in one embodiment, the composition may contain at least two, such as at least three of sodium benzoic, sodium dehydroacetate, potassium sorbate, and phenoxyethanol.

As described above, the preservative enhancing agent can be present in the wiping composition in relatively low amounts. For example, the preservative enhancing agent can be present in the wiping composition in an amount less than about 1% by weight, such as less than about 0.5% by weight, such as less than about 0.4% by weight, such as less than about 0.3% by weight, such as less than about 0.2% by weight, such as less than about 0.1% by weight. The preservative enhancing agent is generally present in an amount greater than about 0.001% by weight, such as greater than about 0.01% by weight, such as greater than about 0.05% by weight. In one embodiment, the preservative enhancing agent is present in the wiping composition in an amount from about 0.1% by weight to about 0.45% by weight.

Of particular advantage, the preservative enhancing agent can be combined with the gluconolactone and a benzoic acid or salt thereof such that the gluconolactone is also present in the composition at relatively minor amounts. For example, the wiping composition can contain a gluconolactone (such as δ-gluconolactone) and can be present in the wiping composition in an amount less than about 1.2% by weight, such as less than about 1% by weight, such as less than about 0.9% by weight, such as less than about 0.8% by weight, such as less than about 0.7% by weight, such as less than about 0.6% by weight, such as in an amount less than about 0.5% by weight. The gluconolactone is generally present in the wiping composition in an amount greater than about 0.05% by weight, such as an amount greater than about 0.1% by weight, such as an amount greater than about 0.2% by weight. In one embodiment, a gluconolactone is present in the wiping composition in an amount from about 0.75% to about 0.2% by weight.

The preservative enhancing agent is present in conjunction with the gluconolactone generally at a weight ratio of from about 5:1 to about 1:5, such as from about 2:1 to about 1:2, such as from about 1.5:1 to about 1:1.5.

The benzoic acid or salt thereof can also be present in the wiping composition in relatively low amounts. For example, in one embodiment, the benzoic acid or salt thereof can be present in the wiping composition in an amount from about 1% to about 0.001% by weight, such as from about 0.5% to about 0.05% by weight, such as from about 0.3% to about 0.1% by weight. In one particular embodiment, the benzoic acid or salt thereof comprises sodium benzoate. The benzoic acid or salt thereof is present in conjunction with the gluconolactone generally at a weight ratio of from about 5:1 to about 1:5, such as from about 4:1 to about 1:4, such as from about 3:1 to about 1:3, such as from about 2:1 to about 1:2, such as from about 1.5:1 to about 1:1.5.

The gluconolactone, benzoic acid or salt thereof, and the preservative enhancing agent form a preservative composition that is contained within the wiping composition. In one embodiment, the preservative composition may contain the gluconolactone in an amount from about 0.75% to about 0.2% by weight. The preservative composition may contain benzoic acid or salt thereof in an amount from about 0.3% to about 0.1% by weight. The preservative composition may contain the preservative enhancing composition in an amount from about 0.1% by weight to about 0.45% by weight.

In addition to the preservative enhancing agent, benzoic acid or salt thereof, and the gluconolactone, the preservative composition may also contain various other components and ingredients. For example, the preservative composition can also contain a gluconate salt, such as calcium gluconate. Gluconolactone is an ester of gluconic acid, while calcium gluconate is a salt of gluconic acid. Other salts of gluconic acid that may be present in the preservative composition include barium gluconate, magnesium gluconate, manganese gluconate, potassium gluconate, sodium gluconate, zinc gluconate, and mixtures thereof. A gluconate can be present in the wiping composition at very low levels. For instance, a gluconate may be present in the wiping composition in an amount less than about 0.5% by weight, such as in an amount less than about 0.05% by weight, such as in an amount less than about 0.01% by weight. One or more gluconates may be present in the wiping composition in an amount greater than about 0.0001% by weight.

In addition to the preservative composition of the present disclosure, the wiping composition can contain various other components and ingredients. For example, the wiping composition can contain a solvent, such as water. Water is generally purified water, including distilled water or deionized water. In addition to water, other solvents may be used, including organic solvents such as lower alcohols and glycols. Exemplary lower alcohols include ethanol, and isopropyl alcohol. Exemplary glycols include 1,2-propanediol, 1,3-propanediol, 1,2-hexanediol, 1,2-octanediol, 1,2-pentanediol, 1,5-pentanediol, and 1,3-butanediol. Further, propanediol derivatives, such as methylpropanediol can be used as a glycol a solvent. The limit to the amount of organic solvent used is dependent on the formulations final use. When present, an organic solvent, such as an alcohol or glycol, may be present in the wiping solution in an amount less than about 5% by weight, such as an amount less than about 3% by weight, such as an amount less than about 1% by weight, such as an amount less than about 0.5% by weight. Water, on the other hand, can generally be present in relatively copious amounts. Water can be present in the wiping composition, for instance, in an amount greater than about 60% by weight, such as an amount greater than about 70% by weight, such as in an amount greater than about 80% by weight, such as in an amount greater than about 85% by weight, such as in an amount greater than about 90% by weight, such as in an amount greater than about 95% by weight. Water is generally present in an amount less than about 99.5% by weight, such as in an amount less than about 98% by weight.

The formulation may further contain additional ingredients, including surfactants, chelators, builder salts, dyes, fragrances and the like. Suitable surfactants include, but are not limited to, non-ionic surfactants, for example, amine oxides, linear alcohol ethoxylates, secondary alcohol ethoxylates, ethoxylate esters, betamines, polyoxyalkylene polymers and copolymers and alkyl polyglycerides. Particular surfactants that may be present in the wiping solution include a glucoside, such as decylglucoside. Another surfactant that may be present in the wiping composition comprises a polysorbate nonionic surfactant, such as a polyoxyethylene sorbitan monolaurate. The polyoxyethylene sorbitan monolaurate may contain from about 10 mols to about 30 mols, such as from about 15 mols to about 25 mols of polyoxyethylene. The surfactants may be present in the final formulation ranges from 0.001 wt. % to 10 wt. %, and more typically in the range being 0.01 to 5 wt. %.

Examples of chelators that may be used are sodium and potassium salts of ethylenediaminetetraacetic acid (EDTA), citric acid, nitriloacetic acid, and various phosphoric acids and zeolites. Chelators serve to remove hardness from the water uses as the solvent. The percentage, by weight, of chelators that may be used in the final formulation ranges from 0.001 wt. % to 10 wt. %, and more typically in the range being 0.01 to 5 wt. %.

Examples of building salts that may be used include sodium metasilicate, sodium tripolyphosphate, sodium nitrilotriacetate, sodium carbonate, sodium silicate, citric acid salts and zeolites. The percentage, by weight, of building salts that may be used in the final formulation ranges from 0.001 to 15 wt. %, with the preferred range being 0.01 to 0.5 wt. %. Other ingredients added to the composition in amounts conventionally used in sanitizing and disinfecting compositions.

In addition to the above, pH adjusting agents may also be present in the composition. For instance, the composition may contain sodium hydroxide and/or citric acid in order to maintain the pH within desired levels.

In one particular embodiment of the present disclosure, the wiping solution contains a glucoside, such as decylglucoside in an amount from about 0.1% to about 2% by weight, such as in an amount from 0.15% to about 0.4% by weight. The composition may also contain a polysorbate surfactant, such as a such as a polyoxyethylene sorbitan monolaurate in an amount from about 0.1% to about 1% by weight, such as an amount from about 0.15% to about 0.4% by weight. A citric acid salt, such as sodium citrate can be present in the wiping composition in an amount from about 0.1% to about 4% by weight, such as an amount of from about 0.5% to about 2% by weight. In addition, the wiping composition may contain sodium hydroxide and/or citric acid in order to maintain the pH within desired limits. The preservative composition of the present disclosure can be contained in the wiping solution in an amount from about 0.1 to about 5% by weight, such as from about 0.5% to about 3% by weight, such as in an amount from about 1% to about 2% by weight. In one embodiment, the preservative composition of the present disclosure is contained in the wiping composition in an amount up to about 1.5% by weight. The remainder of the wiping composition can comprise one or more solvents, such as water.

Once the wiping composition is formulated, the wiping composition is applied to a substrate.

The formulation of the present disclosure may be applied to a substrate to be treated using conventional application techniques. Conventional techniques include spraying, pouring, squirting and/or wiping the formulation on a substrate. The composition is provided to the end user as a ready-to-use formulation or is provided to the end user in a container with an application means. For example, the composition may be provided in a container which is pressurized as an aerosol, a container with a trigger or pump sprayer, as a squirt container or conventional containers with a removable cap that allows the user to pour the formulation onto a substrate.

However, one particularly useful application means is to impregnate the formulation into a wiper substrate. In this embodiment, the wipe is a single use wipe that is impregnated with the formulation and is stored in a container that will dispense the wipe to a user. The container with the wipes may contain a single wipe, or several wipes. Suitable containers include a pouch containing a single wipe, such as a moist towelette which is torn open by the user, or may be a pouch with a resealable opening containing several wipes in a stacked fashion or other suitable formation that would allow a single wipe to be removed from the opening at a time. Pouches are generally prepared form a fluid impervious material, such as a film, a coated paper or foil or other similar fluid impervious materials. In another way to dispense wipes of the present invention is to place the wipe in to a fluid impervious container having an opening to access the wipes in the container. Containers may be molded plastic container with lids that are fluid impervious. Generally, the lid will have an opening to access the wipes in the container. The wipe in the container may in a interleaved stacked, such that as a wipe is removed from the container the next wipe is positioned in the opening of the container ready for the user to remove the next wipe. Alternatively, the wipe may be a continuous material which is perforated between the individual wipes of the continuous material. The continuous wipe material with perforations may be in a folded form or may be in a rolled form. Generally, in the rolled form, the wipe material is feed from the center of the rolled material. As with the interleaved stack, as a wipe is removed from the container, the next wipe is positioned in the opening for the use to remove the next wipe, when needed.

Disposable wipes provide advantages over other application vehicles, such as a reusable sponge, rag or the like. Unlike sponges, rags and the like, which are used repeatedly, the impregnated wipe is used a single time and disposed of.

The formulation is impregnated into the wipe such that the wipe is pre-moistened and will express or release the formulation on to the substrate as the wipe is run across the substrate to be treated. Generally, the formulation is saturated into the wipe such that the wipe will release the formulation to the substrate through the wiping action.

Suitable wipe substrates include woven and nonwoven materials. Essentially any nonwoven web material may be used. Exemplary nonwoven materials may include, but are not limited to meltblown, coform, spunbond, airlaid, airlaced, hydroentangled nonwovens, spunlace, bonded carded webs, and laminates thereof. The fibers used to prepare the wipe substrate may be cellulosic fiber, thermoplastic fibers and mixtures thereof. The fibers may also be continuous fibers, discontinuous fibers, staple fibers and mixtures thereof. Basis weights of the nonwoven web may vary from about 12 grams per square meter to 200 grams per square meter or more.

In one embodiment, the substrate impregnated with the wiping composition contains significant amounts of cellulosic fibers. In particular, the wiping composition of the present disclosure is particularly well suited to protecting the cellulose substrate from attack by microorganisms that can contaminate the product. In one particular embodiment, for instance, the substrate may be made from greater than 80%, such as greater than 85%, such as greater than 90%, such as greater than 95%, such as even 100% by weight cellulose fibers. For examples, in one embodiment, the substrate is made from pulp fibers and a binder in an airlaced process. The basis weight of the substrate can be from about 20 gsm to about 100 gsm, such as from about 40 gsm to about 70 gsm, such as from about 50 gsm to about 60 gsm.

Wiping products made according to the present disclosure have numerous uses and applications. The wiping composition of the present disclosure is generally formulated to be mild and gentle while also possessing some antiseptic properties. Thus the wiping composition is particularly well suited for use in cosmetic wipes and baby wipes. It should be understood, however, the composition of the present disclosure can also be formulated to be used as a disinfectant wipe for application to a surface, such as a countertop or a food surface.

When formulated as a disinfectant, the wiping composition may contain various other antimicrobial agents, such as a quaternary ammonium compound.

Once incorporated into the substrate, the resulting wiping product can have a weight ratio of liquid to substrate of from about 5:1 to about 1:1, such as from about 2:1 to about 4:1. In one embodiment, the weight ratio of liquid to substrate is about 3 to 1. The present disclosure may be better understood with reference to the following examples.

EXAMPLE 1

A 28-day preservative efficacy test was performed on wet wipes treated with wet wipe formulations. The ratio of wet wipe formulation to wipe was approximately 3:1. The wet wipe formulations contained surfactants, emulsifiers, pH adjusters, buffers, solvent, and one of the preservative compositions formulated in accordance with the present disclosure. The preservative compositions of samples 1-6 are shown in Table 1.

TABLE 1

Preservative compositions for wet wipe samples 1-6

| Sample No. | Preservative Composition |
|---|---|
| 1 | 0.75% gluconolactone/sodium benzoate (3:1 wt. ratio) |
| 2 | 0.75% gluconolactone/sodium benzoate (3:1 wt. ratio) combined with 0.25% potassium sorbate |
| 3 | 0.75% gluconolactone/sodium benzoate (3:1 wt. ratio) combined with 0.10% sodium dehydroacetate |
| 4 | 0.75% gluconolactone/sodium benzoate (3:1 wt. ratio) combined with 0.10% sodium benzoate |
| 5 | 1.0% gluconolactone/sodium benzoate (3:1 wt. ratio) |
| 6 | None (Control) |

Three sets of wet wipe samples 1-6 were inoculated with three different pools of microorganisms. Pool 1 contained *Staphylococcus aureus* (ATCC 6538), *Escherichia coli* (ATCC 8739), and *Pseudomonas aeruginosa* (ATCC 9027). Pool 2 contained *Burkholderia cepacia* (ATCC 25416). Pool 3 contained *Candida albicans* (ATCC 10231) and *Aspergillus brasiliensis* (ATCC 16404).

Pool recovery and percent reduction was measured in each inoculated wet wipe sample. Counts were taken at 0, 1, 2, 7 and 14 days. Samples were rechallenged with the appropriate pool on day 14 and additional counts taken on 14, 15, 16, 21 and 28 days. Standard wipe preservative test procedures were followed.

Samples 1-6 were initially inoculated with levels of microorganisms to recover $1.5 \times 10^6$ colony forming units (CFU) of Pool 1 microorganisms at Day 0 and then rechallenged to recover $1.2 \times 10^6$ CFU/wipe at Day 14. The results are shown in Table 2.

TABLE 2

Microbial recovery and percent reduction from initial and rechallenge Pool 1 inoculum in Samples 1-6

| Test sample | | Day 0 | Day 1 | Day 2 | Day 7 | Day 14 | Day 14 Rechallenge | Day 15 | Day 16 | Day 21 | Day 28 |
|---|---|---|---|---|---|---|---|---|---|---|---|
| 1 | CFU[1]/wipe | 6.4E+05 | <100 | <100 | <100 | <100 | 1.1E+06 | <100 | <100 | <100 | <100 |
|   | % red[2] | 55.9 | 100.0 | 100.0 | 100.0 | 100.0 | 8.3 | 100.0 | 100.0 | 100.0 | 100.0 |
| 2 | CFU/wipe | 7.2E+05 | <100 | <100 | <100 | <100 | 2.1E+06 | <100 | <100 | <100 | <100 |
|   | % red | 50.3 | 100.0 | 100.0 | 100.0 | 100.0 | NR | 100.0 | 100.0 | 100.0 | 100.0 |
| 3 | CFU/wipe | 9.1E+05 | <100 | <100 | <100 | <100 | 1.6E+06 | <100 | <100 | <100 | <100 |
|   | % red | 37.2 | 100.0 | 100.0 | 100.0 | 100.0 | NR | 100.0 | 100.0 | 100.0 | 100.0 |
| 4 | CFU/wipe | 1.1E+06 | <100 | <100 | <100 | <100 | 9.0E+05 | <100 | <100 | <100 | <100 |
|   | % red | 26.9 | 100.0 | 100.0 | 100.0 | 100.0 | 25.0 | 100.0 | 100.0 | 100.0 | 100.0 |
| 5 | CFU/wipe | 5.0E+05 | 2.0E+02 | <100 | <100 | <100 | 8.5E+05 | 1.2E+04 | <100 | <100 | <100 |
|   | % red | 65.5 | 100.0 | 100.0 | 100.0 | 100.0 | 29.2 | 99.0 | 100.0 | 100.0 | 100.0 |
| 6 | CFU/wipe | 1.1E+06 | 9.3E+06 | >3.0E+07 | >3.0E+07 | >3.0E+07 | >3.0E+07 | >3.0E+07 | >3.0E+07 | >3.0E+07 | >3.0E+07 |
|   | % red | 26.2 | NR | NR | NR | NR | NR | NR | NR | NR | NR |

[1]Colony forming units per wipe
[2]Percent reduction in CFU/wipe
NR = no reduction Samples 1-6 were initially inoculated with levels of microorganisms to recover $1.8 \times 10^6$ CFU/wipe of Pool 2 microorganisms at Day 0 and then rechallenged to recover $1.2 \times 10^6$ CFU/wipe at Day 14. Table 3 shows the recovery and percent reduction for samples with the Pool 2 initial inoculation.

TABLE 3

Microbial recovery and percent reduction from initial and rechallenge Pool 2 inoculum in Samples 1-6

| Test sample | | Day 0 | Day 1 | Day 2 | Day 7 | Day 14 | Day 14 Rechallenge | Day 15 | Day 16 | Day 21 | Day 28 |
|---|---|---|---|---|---|---|---|---|---|---|---|
| 1 | CFU[1]/wipe | 1.4E+06 | <100 | 1.0E+02 | >3.0E+07 | >3.0E+07 | >3.0E+07 | >3.0E+07 | >3.0E+07 | >3.0E+07 | >3.0E+07 |
|   | % red[2] | 17.7 | 100.0 | 100.0 | NR | NR | NR | NR | NR | NR | NR |

TABLE 3-continued

Microbial recovery and percent reduction from initial and rechallenge Pool 2 inoculum in Samples 1-6

| Test sample | | Day 0 | Day 1 | Day 2 | Day 7 | Day 14 | Day 14 Rechallenge | Day 15 | Day 16 | Day 21 | Day 28 |
|---|---|---|---|---|---|---|---|---|---|---|---|
| 2 | CFU/wipe | 8.2E+05 | <100 | 9.5E+03 | <100 | <100 | 1.5E+06 | 3.0E+04 | 1.3E+03 | <100 | <100 |
|   | % red | 53.1 | 100.0 | 99.5 | 100.0 | 100.0 | NR | 97.5 | 99.9 | 100.0 | 100.0 |
| 3 | CFU/wipe | 7.4E+05 | <100 | <100 | <100 | <100 | 9.5E+05 | 3.0E+04 | <100 | <100 | <100 |
|   | % red | 57.7 | 100.0 | 100.0 | 100.0 | 100.0 | 20.8 | 97.5 | 100.0 | 100.0 | 100.0 |
| 4 | CFU/wipe | 9.4E+05 | <100 | <100 | <100 | <100 | 9.3E+05 | 1.0E+02 | <100 | <100 | <100 |
|   | % red | 46.3 | 100.0 | 100.0 | 100.0 | 100.0 | 22.5 | 100.0 | 100.0 | 100.0 | 100.0 |
| 5 | CFU/wipe | 1.1E+06 | 1.2E+03 | 7.6E+03 | >3.0E+07 | >3.0E+07 | >3.0E+07 | >3.0E+07 | >3.0E+07 | >3.0E+07 | >3.0E+07 |
|   | % red | 39.4 | 99.9 | 99.6 | NR | NR | NR | NR | NR | NR | NR |
| 6 | CFU/wipe | 1.6E+06 | 2.5E+07 | >3.0E+07 | >3.0E+07 | >3.0E+07 | >3.0E+07 | >3.0E+07 | >3.0E+07 | >3.0E+07 | >3.0E+07 |
|   | % red | 8.6 | NR | NR | NR | NR | NR | NR | NR | NR | NR |

[1] Colony forming units per wipe
[2] Percent reduction in CFU/wipe
NR = no reduction Samples 1-6 were initially inoculated with levels of microorganisms to recover $1.5 \times 10^5$ CFU/wipe of Pool 3 microorganisms at Day 0 and then rechallenged to recover $1.4 \times 10^5$ CFU/wipe at Day 14. The results are shown in Table 4.

TABLE 4

Microbial recovery and percent reduction from initial and rechallenge Pool 3 inoculum in Samples 1-6

| Test sample | | Day 0 | Day 1 | Day 2 | Day 7 | Day 14 | Day 14 Rechallenge | Day 15 | Day 16 | Day 21 | Day 28 |
|---|---|---|---|---|---|---|---|---|---|---|---|
| 1 | CFU/wipe | 1.3E+05 | 2.3E+04 | 8.6E+03 | <100 | <100 | 7.8E+04 | 4.9E+04 | 9.3E+03 | <100 | <100 |
|   | % red | 13.3 | 84.7 | 94.3 | 100.0 | 100.0 | 44.3 | 65.0 | 93.4 | 100.0 | 100.0 |
| 2 | CFU/wipe | 1.5E+05 | <100 | <100 | <100 | <100 | 1.0E+05 | 4.7E+03 | <100 | <100 | <100 |
|   | % red | NR | 100.0 | 100.0 | 100.0 | 100.0 | 26.4 | 96.6 | 100.0 | 100.0 | 100.0 |
| 3 | CFU/wipe | 1.0E+05 | 2.3E+04 | 1.0E+02 | <100 | <100 | 1.1E+05 | 5.2E+04 | 1.2E+03 | <100 | <100 |
|   | % red | 33.3 | 84.7 | 99.9 | 100.0 | 100.0 | 22.1 | 62.9 | 99.1 | 100.0 | 100.0 |
| 4 | CFU/wipe | 1.7E+05 | 6.2E+03 | <100 | <100 | <100 | 1.2E+05 | 2.4E+04 | 1.4E+03 | <100 | <100 |
|   | % red | NR | 95.9 | 100.0 | 100.0 | 100.0 | 16.4 | 82.9 | 99.0 | 100.0 | 100.0 |
| 5 | CFU/wipe | 8.0E+04 | 3.4E+04 | 8.4E+03 | <100 | <100 | 1.0E+05 | 4.9E+04 | 1.5E+04 | <100 | <100 |
|   | % red | 46.7 | 77.3 | 94.4 | 100.0 | 100.0 | 27.9 | 65.0 | 89.3 | 100.0 | 100.0 |
| 6 | CFU/wipe | 7.0E+04 | 1.5E+05 | 1.2E+05 | >3.0E+06 | >3.0E+06 | >3.0E+06 | >3.0E+06 | >3.0E+06 | >3.0E+06 | >3.0E+06 |
|   | % red | 53.3 | NR | 18.7 | NR | NR | NR | NR | NR | NR | NR |

[1] Colony forming units per wipe
[2] Percent reduction in CFU/wipe
NR = no reduction

EXAMPLE 2

A 28-day preservative efficacy test was performed on wet wipes treated with preservative compositions formulated in accordance with the present disclosure. Wet wipe samples 7-12 were formulated using Suominen BIOLACE® nonwoven (ALSL55WQ) substrates and a wet wipe formulation. The ratio of wet wipe formulation to wipe was approximately 3:1. The wet wipe formulations contained surfactants, emulsifiers, pH adjusters, buffers, solvent, and one of the preservative compositions, described in Table 5.

TABLE 5

Preservative compositions for wet wipe samples 7-12

| Sample No. | Preservative Composition |
|---|---|
| 7 | 0.50% gluconolactone/sodium benzoate (3:1 wt. ratio) combined with 0.10% potassium sorbate |
| 8 | 0.50% gluconolactone/sodium benzoate (3:1 wt. ratio) combined with 0.10% sodium dehydroacetate |

TABLE 5-continued

Preservative compositions for wet wipe samples 7-12

| Sample No. | Preservative Composition |
|---|---|
| 9 | 0.60% gluconolactone/sodium benzoate (3:1 wt. ratio) combined with 0.10% sodium benzoate |
| 10 | 0.50% gluconolactone/sodium benzoate (3:1 wt. ratio) combined with 0.10% sodium benzoate |
| 11 | 0.50% gluconolactone/sodium benzoate (3:1 wt. ratio) combined with 0.35% phenoxyethanol |
| 12 | None (Control) |

Three sets of wet wipe samples 7-12 were inoculated with three different pools of microorganisms. Pool 1 contained *Staphylococcus aureus* (ATCC 6538), *Escherichia coli* (ATCC 8739), and *Pseudomonas aeruginosa* (ATCC 9027). Pool 2 contained *Burkholderia cepacia* (ATCC 25416). Pool 3 contained *Candida albicans* (ATCC 10231) and *Aspergillus brasiliensis* (ATCC 16404).

Pool recovery and percent reduction was measured in each inoculated wet wipe sample. Counts were taken at 0, 1, 2, 7 and 14 days. Samples were rechallenged with the appropriate pool on day 14 and additional counts taken on 14, 15, 16, 21 and 28 days. Standard wipe preservative test procedures were followed.

Samples 7-12 were initially inoculated with levels of microorganisms to recover $8.90 \times 10^5$ CFU/wipe of Pool 1 microorganisms at Day 0 and then rechallenged to recover $5.0 \times 10^5$ CFU/wipe at Day 14. As illustrated in Table 6, samples 7-11 had above 99% reduction in CFU/wipe at day 7 and day 21. Samples 7-11 did not experience further spikes in microbial growth throughout the remainder of the testing. In comparison, unpreserved sample 12 experienced microbial growth throughout the 28-day testing period.

TABLE 6

Microbial recovery and percent reduction from initial and rechallenge Pool 1 inoculum in Samples 7-12

| Test sample | | Day 0 | Day 1 | Day 2 | Day 7 | Day 14 | Day 14 Rechallenge | Day 15 | Day 16 | Day 21 | Day 28 |
|---|---|---|---|---|---|---|---|---|---|---|---|
| 7 | CFU[1]/wipe | 8.70E+05 | 6.00E+02 | 1.00E+02 | <100 | <100 | 5.60E+05 | 2.20E+03 | <100 | <100 | <100 |
| | % red[2] | 1.69 | 99.93 | 99.99 | 100.0 | 100.0 | NR | 99.56 | 100.0 | 100.0 | 100.0 |
| 8 | CFU/wipe | 9.60E+05 | 5.00E+02 | <100 | <100 | <100 | 5.00E+05 | 4.50E+04 | 3.20E+03 | <100 | <100 |
| | % red | NR | 99.94 | 100.0 | 100.0 | 100.0 | NR | 91.00 | 99.36 | 100.0 | 100.0 |
| 9 | CFU/wipe | 1.05E+06 | 9.00E+03 | <100 | <100 | <100 | 4.90E+05 | 7.00E+04 | 5.20E+03 | <100 | <100 |
| | % red | NR | 98.98 | 100.0 | 100.0 | 100.0 | 2.00 | 86.00 | 98.96 | 100.0 | 100.0 |
| 10 | CFU/wipe | 6.10E+05 | 6.80E+03 | <100 | <100 | <100 | 5.80E+05 | 3.30E+05 | 1.00E+04 | 1.00E+02 | <100 |
| | % red | 31.07 | 99.23 | 100.0 | 100.0 | 100.0 | NR | 34.00 | 98.00 | 99.98 | 100.0 |
| 11 | CFU/wipe | 1.00E+06 | <100 | <100 | <100 | <100 | 4.30E+05 | 2.5E+03 | <100 | <100 | <100 |
| | % red | 12.99 | 100.0 | 100.0 | 100.0 | 100.0 | 14.00 | 99.50 | 100.0 | 100.0 | 100.0 |
| 12 | CFU/wipe | 1.00E+06 | 1.34E+04 | 5.50E+06 | >3.0E+07 | >3.0E+07 | >3.0E+07 | >3.0E+07 | >3.0E+07 | >3.0E+07 | >3.0E+07 |
| | % red | NR | 98.49 | NR | NR | NR | NR | NR | NR | NR | NR |

[1]Colony forming units per wipe
[2]Percent reduction in CFU/wipe
NR = no reduction Table 7 shows the recovery and percent reduction for samples initially inoculated with levels of microorganisms to recover $5.0 \times 10^5$ CFU/wipe of Pool 2 microorganisms at Day 0 and then rechallenged to recover $4.5 \times 10^5$ CFU/wipe at Day 14. Sample 11 experienced above 99% reduction in cfu/mL at day 1 and day 15 without experiencing further spikes in growth. Samples 7-10 and 12 experienced no reduction at week 1; thus, testing was discontinued for those samples prior to the rechallenge.

TABLE 7

Microbial recovery and percent reduction from initial and rechallenge Pool 2 inoculum in Samples 7-12

| Test sample | | Day 0 | Day 1 | Day 2 | Day 7 | Day 14 | Day 14 Rechallenge | Day 15 | Day 16 | Day 21 | Day 28 |
|---|---|---|---|---|---|---|---|---|---|---|---|
| 7 | CFU[1]/wipe | 5.10E+05 | <100 | 3.20E+05 | >3.0E+07 | NP | NP | NP | NP | NP | NP |
| | % red[2] | NR | 100.0 | 36.00 | NR | — | — | — | — | — | — |
| 8 | CFU/wipe | 4.5E+05 | <100 | 7.00E+03 | >3.0E+07 | NP | NP | NP | NP | NP | NP |
| | % red | 10.00 | 100.0 | 98.60 | NR | — | — | — | — | — | — |

TABLE 7-continued

Microbial recovery and percent reduction from initial and rechallenge Pool 2 inoculum in Samples 7-12

| Test sample | | Day 0 | Day 1 | Day 2 | Day 7 | Day 14 | Day 14 Rechallenge | Day 15 | Day 16 | Day 21 | Day 28 |
|---|---|---|---|---|---|---|---|---|---|---|---|
| 9 | CFU/wipe | 4.30E+05 | 3.00E+03 | 6.40E+05 | >3.0E+07 | NP | NP | NP | NP | NP | NP |
|   | % red | 14.00 | 99.40 | NR | NR | — | — | — | — | — | — |
| 10 | CFU/wipe | 4.8E+05 | 1.21E+05 | 5.70E+05 | >3.0E+07 | NP | NP | NP | NP | NP | NP |
|   | % red | 4.00 | 75.80 | NR | NR | — | — | — | — | — | — |
| 11 | CFU/wipe | 5.30E+05 | <100 | <100 | <100 | <100 | 4.20E+05 | <100 | <100 | <100 | <100 |
|   | % red | NR | 100 | 100 | 100 | 100 | 6.67 | 100 | 100 | 100 | 100 |
| 12 | CFU/wipe | 5.30E+05 | 3.60E+07 | 2.75E+07 | >3.0E+07 | NP | NP | NP | NP | NP | NP |
|   | % red | NR | NR | NR | NR | — | — | — | — | — | — |

[1]Colony forming units per wipe
[2]Percent reduction in CFU/wipe
NR = no reduction Samples 7-12 initially inoculated with levels of microorganisms to recover $6.75 \times 10^4$ CFU/wipe of Pool 3 microorganisms at Day 0 were rechallenged to recover $5.75 \times 10^4$ CFU/wipe at day 14. Samples 7-11 experienced above 99% reduction in cfu/mL at day 7 and day 21, a week after both challenges. Samples 7-11 had no spikes in growth throughout the remainder of testing. The results are shown in Table 8.

TABLE 8

Microbial recovery and percent reduction from initial and rechallenge Pool 3 inoculum in Samples 7-12

| Test sample | | Day 0 | Day 1 | Day 2 | Day 7 | Day 14 | Day 14 Rechallenge | Day 15 | Day 16 | Day 21 | Day 28 |
|---|---|---|---|---|---|---|---|---|---|---|---|
| 7 | CFU/wipe | 8.10E+04 | 5.00E+04 | 2.40E+04 | 1.00E+02 | <100 | 5.60E+04 | 3.80E+04 | 1.00E+04 | <100 | <100 |
|   | % red | NR | 25.93 | 64.44 | 99.85 | 100.0 | 2.61 | 33.91 | 82.61 | 100.0 | 100.0 |
| 8 | CFU/wipe | 9.90E+04 | 5.50E+04 | 1.80E+04 | <100 | <100 | 7.00E+04 | 6.00E+04 | 3.50E+04 | <100 | <100 |
|   | % red | NR | 18.52 | 73.33 | 100.0 | 100.0 | NR | NR | 39.13 | 100.0 | 100.0 |
| 9 | CFU/wipe | 5.60E+04 | 2.10E+04 | 3.50E+04 | 2.00E+02 | 1.00E+02 | 6.50E+04 | 2.30E+04 | 9.00E+03 | 8.00E+02 | 1.00E+02 |
|   | % red | 17.04 | 68.89 | 48.15 | 99.70 | 99.85 | NR | 60.00 | 84.35 | 98.61 | 99.83 |
| 10 | CFU/wipe | 8.20E+04 | 4.30E+03 | 5.50E+04 | 2.00E+02 | 1.00E+02 | 5.50E+04 | 1.30E+04 | 1.10E+03 | 1.00E+02 | 1.00E+02 |
|   | % red | NR | 36.30 | 18.52 | 99.70 | 99.85 | 4.35 | 77.39 | 98.09 | 99.83 | 99.83 |
| 11 | CFU/wipe | 1.01E+05 | 4.00E+04 | 1.30E+03 | <100 | <100 | 3.70E+04 | 5.50E+04 | 4.30E+04 | <100 | <100 |
|   | % red | NR | 40.74 | 98.07 | 100.0 | 100.0 | 35.65 | 4.35 | 25.22 | 100.0 | 100.0 |
| 12 | CFU/wipe | 8.70E+04 | >3.0E+06 | >3.0E+06 | >3.0E+06 | >3.0E+06 | >3.0E+06 | >3.0E+06 | >3.0E+06 | >3.0E+06 | >3.0E+06 |
|   | % red | NR | NR | NR | NR | NR | NR | NR | NR | NR | NR |

[1]Colony forming units per wipe
[2]Percent reduction in CFU/wipe
NR = no reduction

EXAMPLE 3

A 28-day preservative efficacy test was performed on wet wipes treated with multiple wet wipe formulations. The wet wipe formulations contained surfactants, emulsifiers, pH adjusters, buffers, solvent, and one of the preservative compositions. In this particular example, preservative formulations were tested that only contained a preservative enhancing agent and were compared against a sample containing both gluconolactone and sodium benzoate and a sample containing no preservative. In this manner, the percent reduction of microorganisms on each inoculated wipe sample due solely to the preservative enhancing agent is illustrated. When the results from Example 3 are compared with the results from Example 1 and Example 2, it is clear that the combination of the preservative composition, comprising gluconolactone and a benzoic acid or salt thereof, and a preservative enhancing agent, has greater efficacy than the individual ingredients alone.

TABLE 9

Preservative Compositions for wet wipe samples 1-6

| Sample No. | Preservative Composition |
|---|---|
| 13 | 0.85% gluconolactone/sodium benzoate |
| 14 | 0.85% Phenoxyethanol |
| 15 | 0.14% Geogard 111S (sodium dehydroacetate) |
| 16 | 0.48% potassium sorbate |

TABLE 9-continued

Preservative Compositions for wet wipe samples 1-6

| Sample No. | Preservative Composition |
|---|---|
| 17 | +0.48% sodium benzoate |
| 18 | None (Control) |

Three sets of wet wipe samples 13-18 were inoculated with three pools of microorganisms. Pool 1 contained *Staphylococcus aureus* (ATCC 6538), *Escherichia coli* (ATCC 8739), and *Pseudomonas aeruginosa* (ATCC 9027). Pool 2 contained *Burkholderia cepacia* (ATCC 25416). Pool 3 contained *Candida albicans* (ATCC 10231) and *Aspergillus brasiliensis* (ATCC 16404).

Pool recovery and percent reduction were measured in each inoculated wet wipe sample. Counts were taken at Day 0, 1, 2, 7 and 14. Samples were rechallenged with the appropriate pool on day 14 and additional counts were taken at Day 14, 15, 16, 21, and 28. Standard wipe preservative test procedures were followed.

Samples 13-18 were initially inoculated with levels of microorganisms to recover $2.82 \times 10^6$ CFU/wipe of Pool 1 microorganisms at Day 0 and then rechallenged to recover $5.0 \times 10^6$ CFU/wipe at Day 14. As illustrated in Table 10, samples 13-17 had above 99% reduction in CPU/wipe at Day 7 and Day 21. Samples 13-17 did not experience a further increase in microbial growth throughout the remainder of the testing. In comparison, unpreserved sample 18 experienced microbial growth throughout the 28-day testing period.

TABLE 10

Microbial recovery and percent reduction from initial and rechallenge Pool 1 inoculum in Samples 13-18.

| Test sample | | Day 0 | Day 1 | Day 2 | Day 7 | Day 14 | Day 14 Rechallenge | Day 15 | Day 16 | Day 21 | Day 28 |
|---|---|---|---|---|---|---|---|---|---|---|---|
| 13 | CFU[1]/wipe | 1.60E+06 | 4.80E+06 | <10 | <10 | <10 | 3.00E+06 | 1.00E+05 | <10 | <10 | <10 |
|    | % red[2] | 43.26 | 98.30 | >99.9 | >99.9 | >99.0 | 40.00 | 98.00 | >99.9 | >99.9 | >99.9 |
| 14 | CFU/wipe | 1.55E+06 | 3.30E+04 | <10 | <10 | <10 | 2.80E+04 | 7.80E+04 | <10 | <10 | <10 |
|    | % red | 45.04 | 98.83 | >99.9 | >99.9 | >99.9 | 44.00 | 98.44 | >99.9 | >99.9 | >99.9 |
| 15 | CFU/wipe | 1.10E+06 | 3.20E+05 | 1.05E+04 | <10 | <10 | 1.60E+06 | 5.80E+05 | 1.50E+05 | <10 | <10 |
|    | % red | 60.99 | 88.65 | 99.63 | >99.9 | >99.9 | 68.00 | 88.40 | 97.00 | >99.9 | >99.9 |
| 16 | CFU/wipe | 1.30E+06 | <10 | <10 | <10 | <10 | 1.05E+06 | <10 | <10 | <10 | <10 |
|    | % red | 53.90 | >99.9 | >99.9 | >99.9 | >99.9 | 79.00 | >99.9 | >99.9 | >99.9 | >99.9 |
| 17 | CFU/wipe | 1.35E+06 | <10 | <10 | <10 | <10 | 1.70E+06 | <10 | <10 | <10 | <10 |
|    | % red | 52.13 | >99.9 | >99.9 | >99.9 | >99.9 | 66.00 | >99.9 | >99.9 | >99.9 | >99.9 |
| 18 | CFU/wipe | 1.80E+06 | 1.10E+06 | TNTC | TNTC | TNTC | TNTC | TNTC | TNTC | TNTC | TNTC |
|    | % red | 36.17 | 60.99 | NR | NR | NR | NR | NR | NR | NR | NR |

[1]Colony forming units per wipe
[2]Percent Reduction in CFU/wipe
TNTC = Too numerous to count
NR = no reduction Table 11 shows the recovery and percent reduction for samples initially inoculated with levels of microorganisms to recover $5.8 \times 10^6$ CFU/wipe of Pool 2 microorganisms at Day 0 and then rechallenged to recover $4.4 \times 10^6$ CFU/wipe at Day 14.

TABLE 11

Microbial recovery and percent reduction from initial rechallenge Pool 2 inoculum in Samples 13-18

| Test sample | | Day 0 | Day 1 | Day 2 | Day 7 | Day 14 | Day 14 Rechallenge | Day 15 | Day 16 | Day 21 | Day 28 |
|---|---|---|---|---|---|---|---|---|---|---|---|
| 13 | CFU[1]/wipe | 1.50E+06 | 3.50E+06 | 3.00E+05 | 3.00E+06 | 3.00E+06 | 3.00E+06 | 3.00E+06 | 3.00E+05 | 3.60E+06 | 2.7E+06 |
|    | % red[2] | 73.91 | 93.91 | 94.78 | 47.83 | 47.83 | 31.03 | 31.03 | 93.10 | 17.24 | 39.08 |
| 14 | CFU/wipe | 1.47E+06 | 2.00E+04 | <10 | 9.60E+03 | 8.00E+03 | 1.20E+03 | 1.20E+05 | 1.34E+04 | 3.30E+03 | <10 |
|    | % red | 74.43 | 99.65 | >99.9 | 99.83 | 99.86 | 72.41 | 97.24 | 99.69 | 99.92 | >99.9 |
| 15 | CFU/wipe | 1.62E+06 | TNTC | TNTC | TNTC | TNTC | TNTC | TNTC | TNTC | TNTC | TNTC |
|    | % red | 71.83 | — | — | — | — | — | — | — | — | — |
| 16 | CFU/wipe | 2.00E06 | <10 | <10 | 2.00E+03 | 1.10E+04 | 1.00E+06 | 2.50E+04 | 1.13E+04 | 2.90E+05 | TNTC |
|    | % red | 65.22 | >99.9 | >99.9 | 99.97 | 99.81 | 77.01 | 99.43 | 99.74 | 93.33 | — |

TABLE 11-continued

Microbial recovery and percent reduction from initial rechallenge
Pool 2 inoculum in Samples 13-18

| Test sample | | Day 0 | Day 1 | Day 2 | Day 7 | Day 14 | Day 14 Rechallenge | Day 15 | Day 16 | Day 21 | Day 28 |
|---|---|---|---|---|---|---|---|---|---|---|---|
| 17 | CFU/wipe | 1.20E+06 | <10 | <10 | <10 | <10 | 1.00E+06 | <10 | <10 | 2.00E+03 | <10 |
|  | % red | 79.13 | >99.9 | >99.9 | >99.9 | >99.9 | 77.01 | >99.9 | >99.9 | 99.95 | >99.9 |
| 18 | CFU/wipe | 2.00E+06 | TNTC | TNTC | TNTC | TNTC | TNTC | TNTC | TNTC | TNTC | TNTC |
|  | % red | 65.22 | NR | NR | NR | NR | NR | NR | NR | NR | NR |

[1] Colony forming units per wipe
[2] Percent reduction in CFU/wipe
TNTC = too numerous to count
NR = no reduction Samples 13-18 initially inoculated with levels of microorganisms to recover $1.0 \times 10^5$ CFU/wipe of Pool 3 microorganisms at Day 0 were rechallenged to recover $2.1 \times 10^5$ CFU/wipe at day 14. The results are shown in Table 12.

TABLE 12

Microbial recovery and percent reduction from initial and rechallenge
Pool 3 inoculum in Samples 13-18.

| Test sample | | Day 0 | Day 1 | Day 2 | Day 7 | Day 14 | Day 14 Rechallenge | Day 15 | Day 16 | Day 21 | Day 28 |
|---|---|---|---|---|---|---|---|---|---|---|---|
| 13 | CFU/wipe | 4.00E+05 | 1.50E+05 | 3.80E+04 | 4.30E+03 | 1.00E+03 | 1.00E+05 | 3.30E+04 | 3.80E+03 | 7.50E+03 | 5.00E+03 |
|  | % red | NR | 50.00 | 62.00 | 95.70 | 99.00 | 52.38 | 84.29 | 98.19 | 96.43 | 97.6 |
| 14 | CFU/wipe | 3.00E+05 | 6.00E+04 | 5.30E+04 | 1.00E+04 | 3.10E+03 | 8.90E+04 | 6.00E+04 | 8.00E+03 | 7.60E+03 | 1.60E+04 |
|  | % red | NR | 40.00 | 47.00 | 90.00 | 96.90 | 57.62 | 71.43 | 96.19 | 93.38 | 92.4 |
| 15 | CFU/wipe | 2.60E+05 | 4.10E+04 | 3.60E+04 | 9.70E+03 | 6.70E+03 | 1.00E+05 | 4.20E+04 | 1.20E+04 | 3.20E+04 | 3.40E+04 |
|  | % red | NR | 59.00 | 64.00 | 90.30 | 93.30 | 52.38 | 80.00 | 94.29 | 84.76 | 83.8 |
| 16 | CFU/wipe | 2.60E+05 | 4.10E+04 | 2.00E+02 | <10 | <10 | 7.90E+04 | 2.10E+04 | 5.00E+02 | 1.00E+02 | <100 |
|  | % red | NR | 59.00 | 99.80 | >99.9 | >99.9 | 62.38 | 90.00 | 99.76 | 99.95 | >99.9 |
| 17 | CFU/wipe | 4.70E+05 | 2.80E+04 | 2.20E+03 | 1.00E+02 | <10 | 6.50E+04 | 1.60E+04 | 5.00E+02 | 2.00E+02 | <100 |
|  | % red | NR | 72.00 | 97.80 | 99.90 | >99.9 | 69.05 | 92.38 | 99.76 | 99.90 | >99.9 |
| 18 | CFU/wipe | 4.20E+05 | TNTC | TNTC | TNTC | TNTC | TNTC | TNTC | TNTC | TNTC | TNTC |
|  | % red | NR | NR | NR | NR | NR | NR | NR | NR | NR | NR |

[1] Colony forming units per wipe
[2] Percent reduction in CFU/wipe
TNTC = too numerous to count
NR = no reduction These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:
1. A wiping product comprising:
a liquid absorbent substrate; and
a wiping composition comprising a preservative composition for preserving the liquid absorbent substrate and the wiping composition, the preservative composition comprising gluconolactone, a benzoic acid or salt thereof, and a preservative enhancing agent, the preservative enhancing agent comprising a phenolether, an organic acid, or a salt of an organic acid, the organic acid or the salt of an organic acid having a carbon chain length of from about 6 carbon atoms to about 8 carbon atoms, the organic acid or the salt of an organic acid being either cyclic or acyclic, wherein the preservative enhancing agent and the gluconolactone are present in the wiping composition at a weight ratio of from about 5:1 to about 1:5.625, and the benzoic acid or salt thereof and the gluconolactone are present in the wiping composition at a weight ratio of from about 5:1 to about 1:5, and wherein the preservative enhancing agent is present in the wiping composition in an amount less than about 1% by weight.

2. A wiping product as defined in claim 1, wherein the preservative composition is present in the wiping composition in an amount sufficient for the composition to inhibit, kill, and/or destroy one or more microorganisms.

3. A wiping product as defined in claim 1, wherein the preservative enhancing agent is present in the wiping composition in an amount sufficient for the composition to inhibit, kill, or destroy *Staphylococcus aureus, Escherichia* coli, *Pseudomonas aeruginosa, Candida albicans, Burkholderia cepacia* and/or *Aspergillus brasiliensis*.

4. A wiping product as defined in claim 3, wherein the preservative enhancing agent is present in the wiping composition in an amount sufficient for the composition to kill, inhibit, and/or destroy *Burkholderia cepacia*.

5. A wiping product as defined in claim 1, wherein the liquid absorbent substrate comprises a nonwoven web.

6. A wiping product as defined in claim 1, wherein the wiping composition further comprises a gluconate salt.

7. A wiping product as defined in claim 1, wherein the preservative enhancing agent comprises the phenolether and the phenolether comprises phenoxyethanol.

8. A wiping product as defined in claim 1, wherein the benzoic acid or salt thereof comprises sodium benzoate.

9. A wiping product as defined in claim 1, wherein the preservative enhancing agent is present in the wiping composition in an amount less than 0.5% by weight.

10. A wiping product as defined in claim 1, wherein the gluconolactone is present in the wiping composition in an amount from about 0.75% by weight to about 0.2% by weight.

11. A wiping product as defined in claim 1, wherein the benzoic acid or salt thereof is present in the wiping composition in an amount from about 0.5% by weight to about 0.05% by weight.

12. A wiping product as defined in claim 1, wherein the wiping composition further contains a solvent.

13. A wiping product as defined in claim 10, wherein the solvent comprises, water, an organic solvent, or mixtures thereof.

14. A wiping product as defined in claim 1, wherein the wiping composition further comprises one or more surfactants, chelators, builder salts, dyes, or fragrances.

15. A wiping product as defined in claim 1, wherein the liquid absorbent substrate is saturated with the wiping composition.

16. A wiping product as defined in claim 10, wherein the solvent comprises a mixture of water and an alcohol or comprises a mixture of water and a glycol.

17. A wiping product as defined in claim 16, wherein the glycol comprises 1,2-propanediol, 1,3-propanediol, 1,2-hexanediol, 1,2-octanediol, 1,2-pentanediol, 1,5-pentanediol, 1,3-butanediol, or propanediol derivatives thereof.

18. A wiping product as defined in claim 1, wherein the liquid absorbent substrate comprises a meltblown web, a coform web, a spunbond web, an airlaid web, an airlaced web, a hydroentagled web, a bonded card web, or laminates thereof.

19. A wiping product as defined in claim 1, wherein the preservative enhancing agent comprises sodium dehydroacetate.

20. A wiping product as defined in claim 1, wherein the preservative enhancing agent comprises potassium sorbate.

21. A wiping product as defined in claim 1, wherein the preservative enhancing agent comprises a mixture containing at least two preservative enhancing agents selected from the group consisting of phenoxyethanol, sodium dehydroacetate and potassium sorbate.

22. A wiping product comprising:
a liquid absorbent substrate; and
a wiping composition comprising a preservative composition, the preservative composition comprising gluconolactone, a benzoic acid or salt thereof, and a preservative enhancing agent, the preservative enhancing agent comprising a phenolether, an organic acid, or a salt of an organic acid, the organic acid or the salt of an organic acid having a carbon chain length of from about 6 carbon atoms to about 8 carbon atoms, the organic acid or the salt of an organic acid being either cyclic or acyclic, wherein the preservative composition does not contain a quaternary ammonium compound, and wherein the preservative enhancing agent is present in the wiping composition in an amount less than about 1% by weight.

23. A wiping product as defined in claim 22, wherein the wiping composition comprises a disinfectant, and wherein the disinfectant comprises an antimicrobial agent.

\* \* \* \* \*